United States Patent
Li et al.

(10) Patent No.: US 9,752,137 B2
(45) Date of Patent: Sep. 5, 2017

(54) COMPOUNDS, COMPOSITIONS AND METHODS FOR THE PREPARATION OF PEPTIDE/PROTEIN CONJUGATES

(71) Applicant: The University of Hong Kong Shenzhen Institute of Research and Innovation, Shenzhen, Nanshan (CN)

(72) Inventors: Xuechen Li, Hong Kong (CN); Chun Ling Tung, Hong Kong (CN); Clarence Tsun Ting Wong, Hong Kong (CN)

(73) Assignee: THE UNIVERSITY OF HONG KONG SHENZHEN INSTITUTE OF RESEARCH AND INNOVATION, Shenzhen (CN)

( * ) Notice: Subject to any disclaimer, the term of this patent is extended or adjusted under 35 U.S.C. 154(b) by 43 days.

(21) Appl. No.: 14/727,163

(22) Filed: Jun. 1, 2015

(65) Prior Publication Data
US 2016/0333115 A1 Nov. 17, 2016

(30) Foreign Application Priority Data

May 11, 2015 (CN) .......................... 2015 1 0236410

(51) Int. Cl.
| | | |
|---|---|---|
| *C07K 7/06* | (2006.01) | |
| *C12N 9/82* | (2006.01) | |
| *C07K 14/765* | (2006.01) | |

(52) U.S. Cl.
CPC ................ *C12N 9/82* (2013.01); *C07K 7/06* (2013.01); *C07K 14/765* (2013.01); *C12Y 305/01001* (2013.01)

(58) Field of Classification Search
None
See application file for complete search history.

(56) References Cited

U.S. PATENT DOCUMENTS

| | | | |
|---|---|---|---|
| 8,604,127 B2* | 12/2013 | Lee ................. | A61K 47/48215 424/179.1 |
| 8,795,680 B2 | 8/2014 | Kubler-Kielb et al. | |
| 2016/0281111 A1* | 9/2016 | Cotta-Ramusino ...... | C12N 9/22 |

FOREIGN PATENT DOCUMENTS

WO 2010120365 A2 10/2010

OTHER PUBLICATIONS

De Cesco et al. Journal of Medicinal Chemistry 55(14): 6306-6315 (2012) Abstract only.*

* cited by examiner

*Primary Examiner* — Anand Desai
(74) *Attorney, Agent, or Firm* — Leason Ellis LLP (57) ABSTRACT

Compounds, compositions and methods for the preparation of peptide/protein conjugates, said method comprising a step of reacting a compound (2) represented by the formula (2) with a compound (3) represented by the formula (3) to obtain compound (1) represented by the formula (1), wherein R' represents substituent, and R represents H or at least one substituents. Also disclosed is a kit comprising the compound.

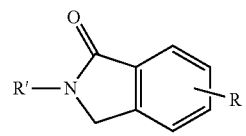

(1)

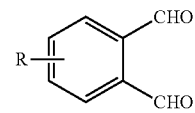

(2)

(3)

10 Claims, 9 Drawing Sheets

Fig. 1

R = substituent

COMPOUNDS, COMPOSITIONS AND METHODS FOR THE PREPARATION OF PEPTIDE/PROTEIN CONJUGATES

RELATED APPLICATIONS

This application claims priority under 35 U.S.C. §119 to Chinese application serial No. 201510236410.0, filed May 11, 2015, which is hereby incorporated by reference in its entirety.

1. FIELD

Disclosed herein are compounds, compositions and methods for the preparation of peptide/protein conjugates. This disclosure further relates to methods to label and modify unprotected peptides and native proteins, and to prepare protein conjugates with poly(ethylene glycol)s (PEGs), small molecules, probes, or other suitable agents.

2. BACKGROUND

Protein labeling provides valuable tools for studying the function of the intracellular protein such as immunostaining and immunolocalization, and developing therapeutic biologics which include poly(ethylene glycol)-protein conjugate drugs, antibody-drug conjugates (ADC), carbohydrate-protein conjugate vaccines and so on. Native protein labeling often involves the conjugation chemistry to take place at the nucleophilic side chains of the amino acids of the protein under the physiological conditions, among which lysine and cysteine are the most common labeling site. Conjugation at primary amine of the lysine residue and the N-terminus involves using acyl donors as the labeling reagents, which are listed as below.

In particular, acyl succinimidyl succinate method using NHS-ester (i.e., N-hydroxysuccinimide) is widely used strategy to label the primary amine, e.g. Lysine, as shown in the below picture (Basle, et al. *Chem. Biol.* 2013, 17, 213).

In the current method of protein labeling, scientists often encounter the problem of stability, solubility, and reactivity of the substrate, and the generation of by-products. For example, the amine-reactive groups like NHS-ester and anhydride are easily hydrolyzed under the physiological buffer such that the reactivity would be affected. The reaction condition is also critical to protein conjugation, wherein pH, solvents and temperature are specific for different labeling reagents. Furthermore, the byproducts (e.g., NHS) are generated after the conjugation reaction that requires further purification. Some of the by-products are even toxic to cells. In this regard, a traceless labeling method would be desired.

The aryl ortho dialdehyde, the common example as o-phthaldialdehyde (OPA), is a well-known fluorescent reagent used to detect primary amines, which has not been used previously to prepare protein conjugates. Furthermore, the existing reaction requires either the thiol or cyanide as the third reacting component and the generated product is 2H-isoindole compounds.

-continued

2H-Isoindole compounds

Wherein R and R' represents any substituent.

3. SUMMARY

The present disclosure relates to compounds, compositions and methods for preparation of peptide/protein conjugates. The preparation of peptide/protein conjugates often relies on the reaction to use the nucleophilic side chains of amino acids (e.g., lysine, serine, threonine, and cysteine) within peptides and proteins; thus the conjugate method require electrophilic donors as the reacting partners. In addition, the conjugate reaction needs to be compatible with the aqueous buffer in order to maintain the function of the proteins. The presently disclosed method is a traceless, simple and rapid strategy to label and modify peptide/proteins at the lysine site and the N-terminus under the aqueous buffer condition (pH 3-9).

In one embodiment, a method is provided for the preparation of a compound (1) represented by the formula (1), said method comprising a step of reacting a compound (2) represented by the formula (2) with a compound (3) represented by the formula (3):

(1)

R'—NH$_2$ (2)

(3)

Wherein R' represents substituent, and R represents H or at least one substituents. As R and R', those skilled in the art may select any suitable substituent as long as it would not affect the reaction. For example, R and R' may independently be aliphatic group, alicyclic groups, aromatic group and the like. Further, R' may be peptide residue and/or protein residue, especially enzyme residue and/or antibodies residue. In the whole description, the peptide residue, protein residue, enzyme residue and/or antibodies residue refer to a peptide, protein, enzyme and/or antibodies with —NH$_2$ at N-terminus or side chain of lysine residue removed.

The present invention provides a method of conjugating a first molecule, such as peptides and proteins, with a second molecule. The second molecule includes, for example, PEGs, lipids, small molecules, carbohydrates, DNAs, enzymes, labels, drugs, biologically active molecules, peptides or proteins. The method has easy operation, mild conditions, and rapid conversion. The present disclosure uses a molecule comprising o-phthaldialdehyde (OPA) which react with primary amine groups (e.g. lysine and the N-terminus) within peptides and proteins, R'—NH$_2$, forming N-substituted isoindolin-1-one compounds. In one embodiment, the structure of N-substituted isoindolini-1-one compound is:

(1)

A molecule comprising OPA is an OPA derivative. One embodiment of an OPA derivative is compound (3) represented by formula (3).

(3)

The disclosed method does not generate any by-product, realizing a traceless bio-conjugation. The disclosed method is conducted under the physiological solution, tolerant of a wide range of pH, for successful conjugation on proteins, peptides, including native and non-native proteins and peptides. The disclosed method does not require any external catalyst or reagent. The method comprises reacting o-phthaldialdehyde (OPA), or its derivatives that comprise various substituents, with a peptide or protein that comprises amino acid residues that have a nucleophilic side chains and an N-terminal residue. One skilled in the art would know suitable OPA derivatives that work well. The OPA derivatives with its various substituents can contain functional groups, including thiol, carboxylic acid, azide, alkyne, ester, ether, alkene, or hydroxyl group, which can conjugate other moieties to the peptide or protein.

Also provided herein is an applicable method for the preparation of the protein conjugates, such as antibody-drug conjugates (ADC), PEGylated proteins and carbohydrate-protein conjugates. For example, the o-phthaldialdehyde derivatized with PEGs, lipids, small molecules, carbohydrates, DNAs, enzymes, peptides or proteins can be used to conjugate with other peptides/protein. The o-phthaldialdehyde derivative and the peptide/protein may be admixed in the reaction solution without using any external catalyst and reagent. The disclosure stated herein is very chemoselective with specific conjugation at the primary amino group of the peptide and protein.

Provided herein is a bio-conjugation method using simple conditions, without requiring any sophisticated chemistry and special care. The disclosed method is easily operative and the working condition is well suitable for native protein conjugations.

Also provided herein is a composition comprising the conjugate produced by the methods provided herein. In certain embodiments, the composition is a therapeutic or a diagnostic composition.

Also provided herein is a kit comprising the composition in the present disclosure.

4.1 DEFINITIONS

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkene" refers to an unsaturated monovalent radical containing carbon and hydrogen, which may be branched, linear, or cyclic. The alkene group may be monounsaturated or polyunsaturated.

An "peptide/protein residue" is preferably an a-amino acid residue (i.e. —CO—CHR—NH—); it may also be a β- or other amino acid residue (e.g. —CO—$CH_2$CHR—NH—), where R is a side chain.

The term "non-natural amino acids" refers to those amino acids not present in proteins found in nature such as beta-alanine (β-Ala) or 6-aminohexanoic acid (Ahx).

The term "label" refers to any identifying tag that may be conjugated to a peptide or protein. A wide variety of labels are known in the art, for a wide variety of different applications. Depending on the specific application, a suitable label for that specific application may be selected. Suitable labels for specific applications are known to the person skilled in the art, and include, but are not limited to, all kinds of fluorophores, biotin, polyethylene glycol (PEG) chains, polypropylene glycol (PPG) chains, mixed polyethylene/polypropylene glycol chains, radioactive isotopes, steroids, pharmaceutical compounds, lipids, peptides, glycans (including oligo- and polysaccharides), nucleotides (including oligo- and polynucleotides) and peptide tags. Examples of suitable peptide tags include FLAG or HIS tags. An example of a suitable glycan is concanavalin. Preferably, the label is selected from the group comprising polyethylene glycol chains, polypropylene glycol chains, mixed polyethylene/polypropylene glycol chains, radioactive isotopes, steroids, pharmaceutical compounds, lipids, peptides, glycans, nucleotides and peptide tags.

5. DETAILED DESCRIPTION

Disclosed herein is a method for preparation of the compound (1) represented by the formula (1), (1)

Wherein R' represents substituent, and R represents H or at least one substituents.

Said compound (1) is prepared by reacting a compound (2) represented by the formula (2) with a compound (3) represented by the formula (3).

In the formula above, R' may be any substituent, especially peptide residue and/or protein residue and R represents. Said peptide residue may be synthetic or natural peptide residue. Said protein residue is native protein residue or recombinant protein residue, or enzyme residue or antibodies residue. Said peptide residue may have at least one lysine residue in the sequence. Said peptide residue may have free N-terminus R may be H or any substituent, preferably selected from alkyl, epoxide, amide, amine, ketone, aldehyde, phosphate, sulfate, halide, nitrile, nitro, azido, thiol, carboxylic acid, alkyne, ester, ether, alkene, or hydroxyl group. Synthetic peptide may contain non-natural amino acids.

Said compound (3) is preferably selected from compounds 1 to 14:

3

4

5

6

7

8

9

10

11

12

13

14

Figure 1:
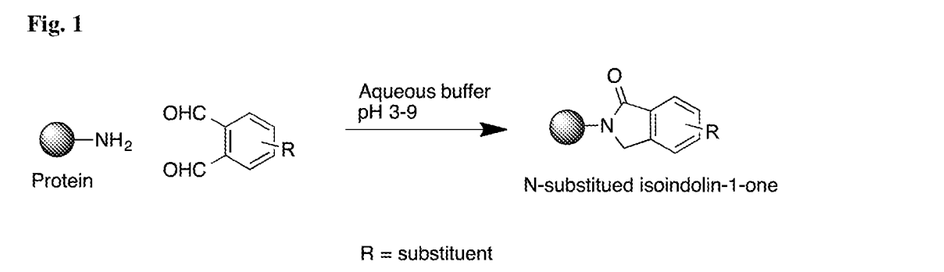
FIG. 1 illustrates the overall principle of OPA/amine-based bio-conjugation.

In particular, disclosed herein is a method of preparation of peptide/protein conjugates. When R' is a peptide residue and/or a protein residue, the compound (1) represented by the formula (1) is a peptide/protein conjugate. Previously, o-phthaldialdehyde (OPA) has been shown to react with primary amine in the presence of a thiol or cyanide to form 2H-isoindole compounds. In one embodiment, OPA and its derivatives directly react with a free amine group in the absence of thiols or cyanides. In certain embodiments, OPA and its derivatives directly react with a free amine group in the absence of thiols or cyanides under wide a range of aqueous buffer solutions ranging from pH 3-9 as well as organic solvents. In one embodiment, the product is an N-substituted isoindolin-1-one compound (FIG. 1). The reaction is extremely rapid, which requires only 10 min to complete (FIG. 2) and is traceless without generation of any byproducts. In one embodiment, a lysine residue is labeled in a peptide or protein. In one embodiment, one or more lysine residues are labeled or modified in a peptide or protein. In certain embodiments, the reaction is much more efficient than other known methods to label the lysine residue within a peptide or protein.

In certain embodiments, 1, 2, 3, 4, 5, 6, 7, 8, 9, 10, 10-15, 15-20, or 20-25 lysine residues are labeled in a peptide or protein. In certain embodiment, the peptide has a length of 2, 3, 4, 5, 6, 7, 8, 9, 10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-200, 200-300, 300-400, 400-500, 500-600, 600-700, 700-800, 800-900, 900-1000, or more than 1000 residues. In certain embodiment, the protein is 1-5, 5-10, 10-20, 20-30, 30-40, 40-50, 50-60, 60-70, 70-80, 80-90, 90-100, 100-150, 150-200, 200-250, 250-300, 300-500 or more than 500 dalton.

Figure 5:
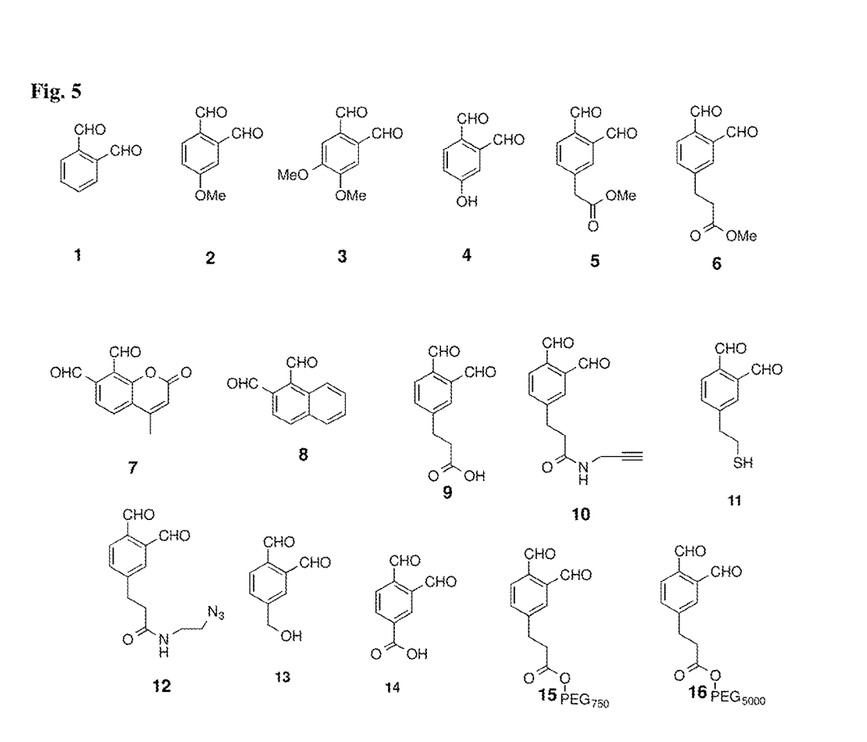
FIG. 5 is representative OPA derivatives.
Figure 6:
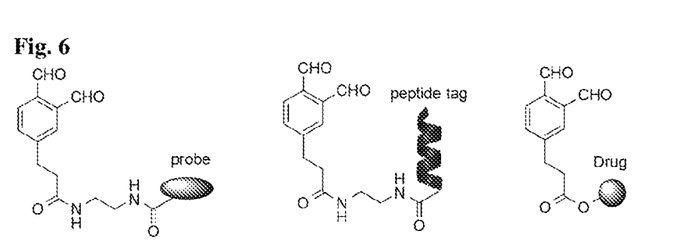
FIG. 6 illustrates the OPA derivatized with peptides, probes, and drugs.

A series of o-phthaldialdehyde derivatives have been synthesized to conjugate with peptides/proteins at the lysine residue with the result of the red-shift of emission of wavelength and giving out blue fluorescence. Some representative OPA derivatives are listed in FIG. 5. Compound 1 (OPA) emits blue fluorescence under UV excitation after conjugation with amines, while compound 2, 3, 5, 7 & 8 emit green fluorescence under excitation of 350 nm.

Figure 4:
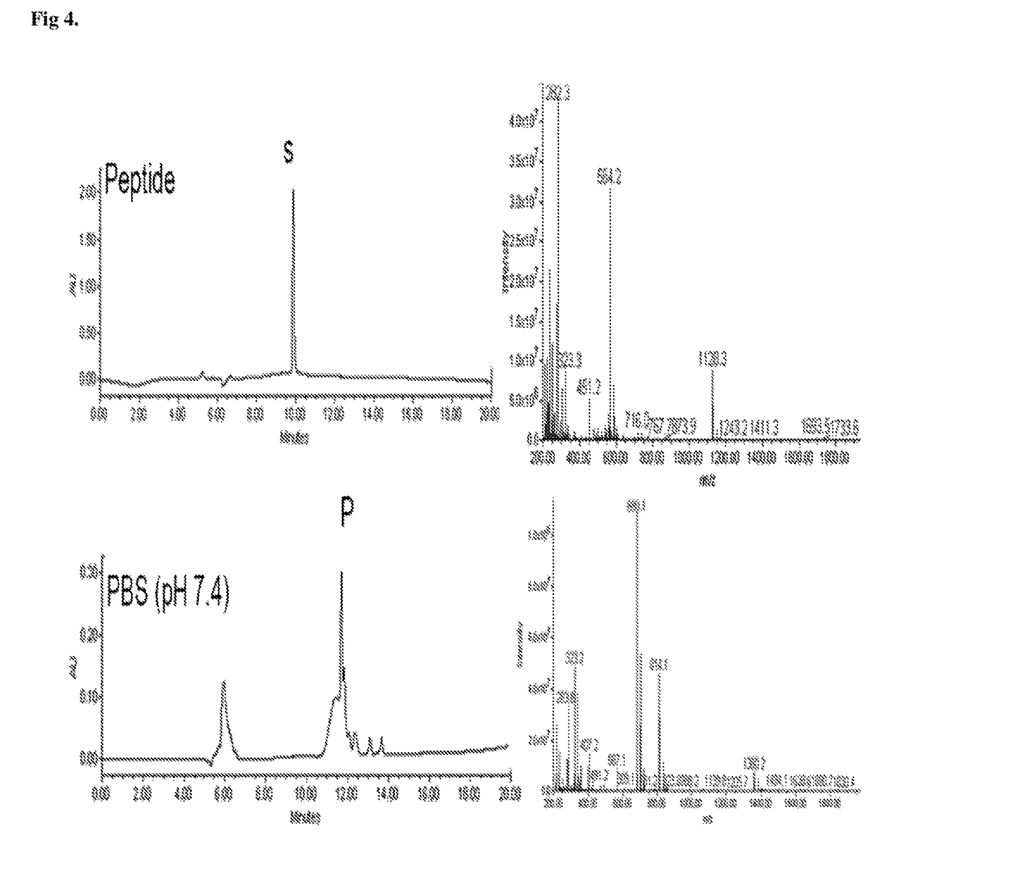
FIG. 4 is LC-MS spectra of the reaction from Example 2.

In particular, compounds 9-14 (FIG. 5) have bi-functional groups which can serve as a good linker to conjugate probes, peptides, PEGs, drugs, etc. to the protein of interest (FIG. 4). In certain embodiments, OPA derivatives have bi-functional groups which can serve as a good linker to conjugate probes, peptides, PEGs, biologically active molecules, etc. In certain embodiment, an OPA derivative comprises a carboxylic acid group or an alkyne group. In one embodiment, different molecules can react with the carboxylic acid group of compound 9. In one embodiment, Compound 10 containing an alkyne group can be used for click chemistry or used as fluorescent probes for imaging. The disclosed method allows the peptide/protein to be conjugated with small molecules, drugs, PEG, lipids, oligosaccharides, nucleic acids or polynucleotides etc. at the primary amine site. In certain embodiments, the presently disclosed methods are high yielding, wide in scope, create only byproducts that can be removed without chromatography, are stereospecific, simple to perform, and can be conducted in easily removable or benign solvents.

Figure 7:
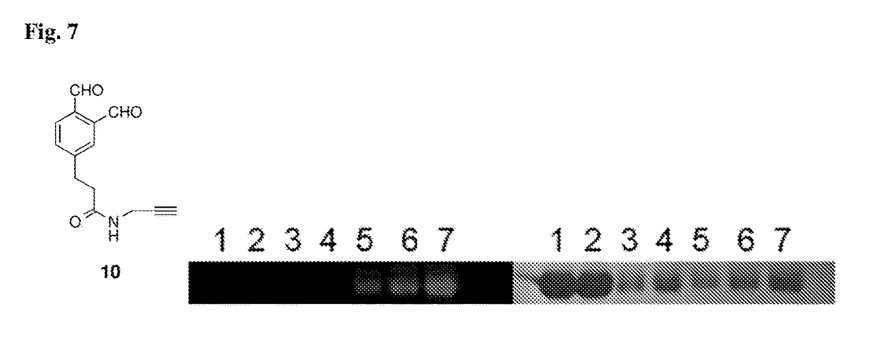
FIG. 7 illustrates the OPA containing an alkyne group can be conjugated to BSA, which is then reacted with azido-rhodamine via click chemistry, wherein, Lane 1 and 2: BSA; Lane 3 and 4: BSA+Compound 10; Lane 5, 6 and 7: BSA+Compound 10+azido-rhodamine with different concentrations (azide-rhodamine only reacts with compound 10 but not BSA)

In one embodiment, conjugate protein samples are formed comprising compound 10. In one embodiment, BSA protein is used to demonstrate the bioconjugation. For example, after incubation of compound 10 with BSA for 1 hr in an aqueous buffer, a rhodamine compound with an azido group was added, which could be reacted with the alkyne group of compound 10 via "click chemistry". The fluorescent signal was recorded after the protein was separated by SDS-PAGE (FIG. 7). The result showed that the BSA was successfully conjugated with compound 10.

Antibody-drug conjugate (ADC) emerges as a new approach to develop conjugated monoclonal antibody with cytotoxic drugs. In one embodiment, the antibody is an antibody against a cancer antigen. In certain embodiments, drugs can be anchored specifically into tumor cells by the monoclonal anticancer drugs by antibody followed by internalization of antibody into tumor cell to prevent unwanted side reaction of the drugs. In one embodiment, compound 9 is derivatized with taxol and conjugated to an anti-cancer antibody.

PEGylation or covalent attachment of poly(ethylene glycol) (PEG) of protein drugs improve their pharmacokinetic properties. PEGylation is a chemical reaction between polyethylene glycol (PEG) to other molecules like drugs or protein. It is a simple method to increase the hydrodynamic size of the molecules and thus enhance the half-lives of peptides and proteins in circulation, and it can also improve the solubility of drug. For example, a PEGylated protein drug is synthesized using PEG succinimidyl succinate. The shortcomings of the succinimidyl succinate method include long reaction time, lack of specificity and generation of NHS as the by-product.

Figure 8:
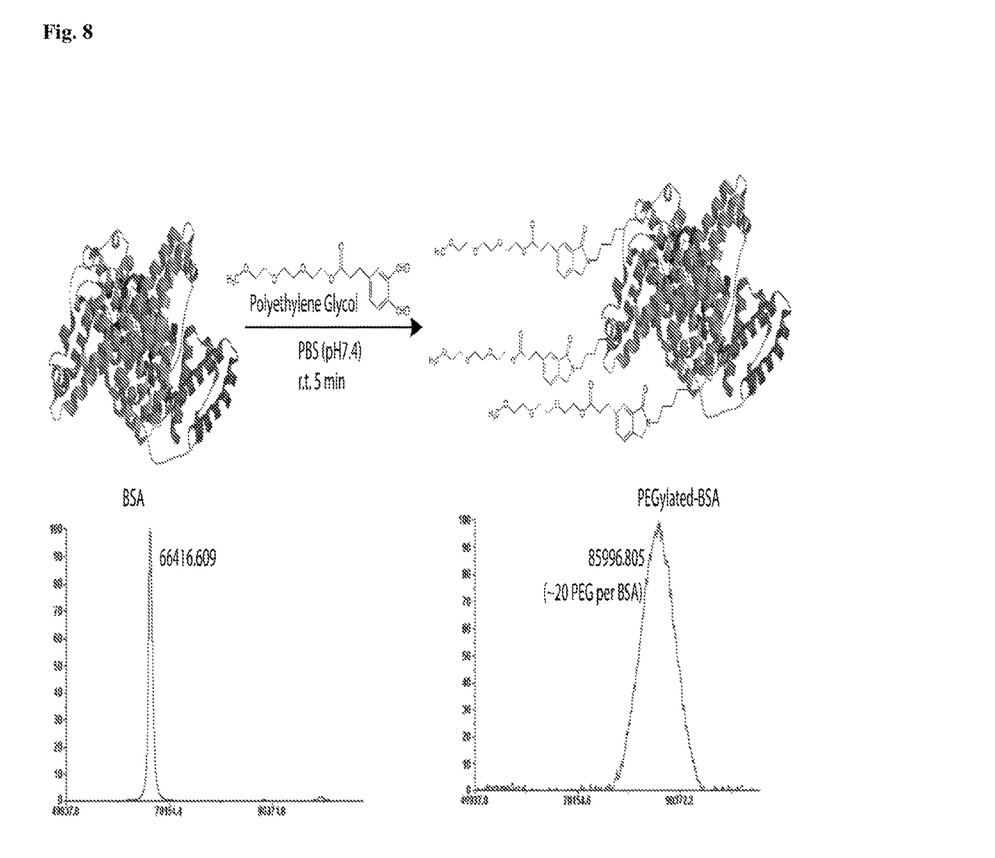
FIG. 8 Illustrate the OPA derivatized with a PEG can be used to conjugated to BSA to form PEGylated proteins.

In one embodiment, the presently disclosed compound is used to react with PEG prior to conjugation. For example, Compound 9 is used to react with a PEG molecule first and then the resultant OPA-PEG ester is conjugated with BSA. This bio-conjugation is completed within 5 min with about 20 PEG molecules in average added to the protein (FIG. 8). In certain embodiments, the disclosed compounds can be used in the PEGylation of adenosine deaminase and L-asparaginase, whose PEG conjugates are approved drugs, namely Adagen and Oncaspar respectively.

Also provided herein is a composition comprising a conjugate produced by the compound described herein. In certain embodiments, the composition further comprises a pharmaceutically acceptable carrier. A wide variety of suitable pharmaceutically acceptable carriers are known in the art (cf. for example R. C. Rowe, P. J. Sheskey and P. J. Weller (Eds.), Handbook of Pharmaceutical Excipients, 4.sup.th Ed. 2003).

In certain embodiments, the disclosed conjugate is joined to a label. In certain embodiments, the conjugate is used in labeling, imaging and/or modification of a molecule.

Applications of the method for the modification of peptide/protein described herein include, but are not limited to, diagnostic and therapeutic applications.

For the use of the conjugated peptide/protein as therapeutics, the conjugates described herein can be found in the form of prodrug, salt, solvate or clathrate, either in an isolated form or in combination with additional active agents. The conjugated peptide/protein can be formulated together with an excipient which is acceptable from the pharmaceutical point of view. Preferred excipients include sugars, starches, celluloses, gums and proteins. In a particular embodiment, the composition will be formulated in a solid pharmaceutical dosage form (for example tablets, capsules, coated tablets, granules, suppositories, crystalline or amorphous sterile solids which can be reconstituted to provide liquid forms etc.), liquid pharmaceutical dosage form (for example solutions, suspensions, emulsions, elixirs, lotions, unguents etc.) or semisolid pharmaceutical dosage form (gels, ointments, creams and the like). The compositions can be administered by any route including, without being limited to, oral, intravenous, intramuscular, intraarterial, intramedullary, intrathecal, intraventricular, transdermal, subcutaneous, intraperitoneal, intranasal, enteral, topical, sublingual or rectal route. A review of the different forms of administration of active ingredients, of the excipients to be used and of the processes for manufacturing them can be found in Tratado de Farmacia Galenica, C. Fauli i Trillo, Luzam 5, S. A. de Ediciones, 1993 and in Remington's Pharmaceutical Sciences (A. R. Gennaro, Ed.), 20th edition, Williams & Wilkins PA, USA (2000). Examples of pharmaceutically acceptable vehicles are known in the state of the art and include phosphate-buffered saline solutions, water, emulsions, such as oil/water emulsions, different types of wetting agents, sterile solutions, etc. The compositions comprising said vehicles can be formulated by conventional processes known in the state of the art.

6. EXAMPLES

6.1 Example 1

Figure 2:
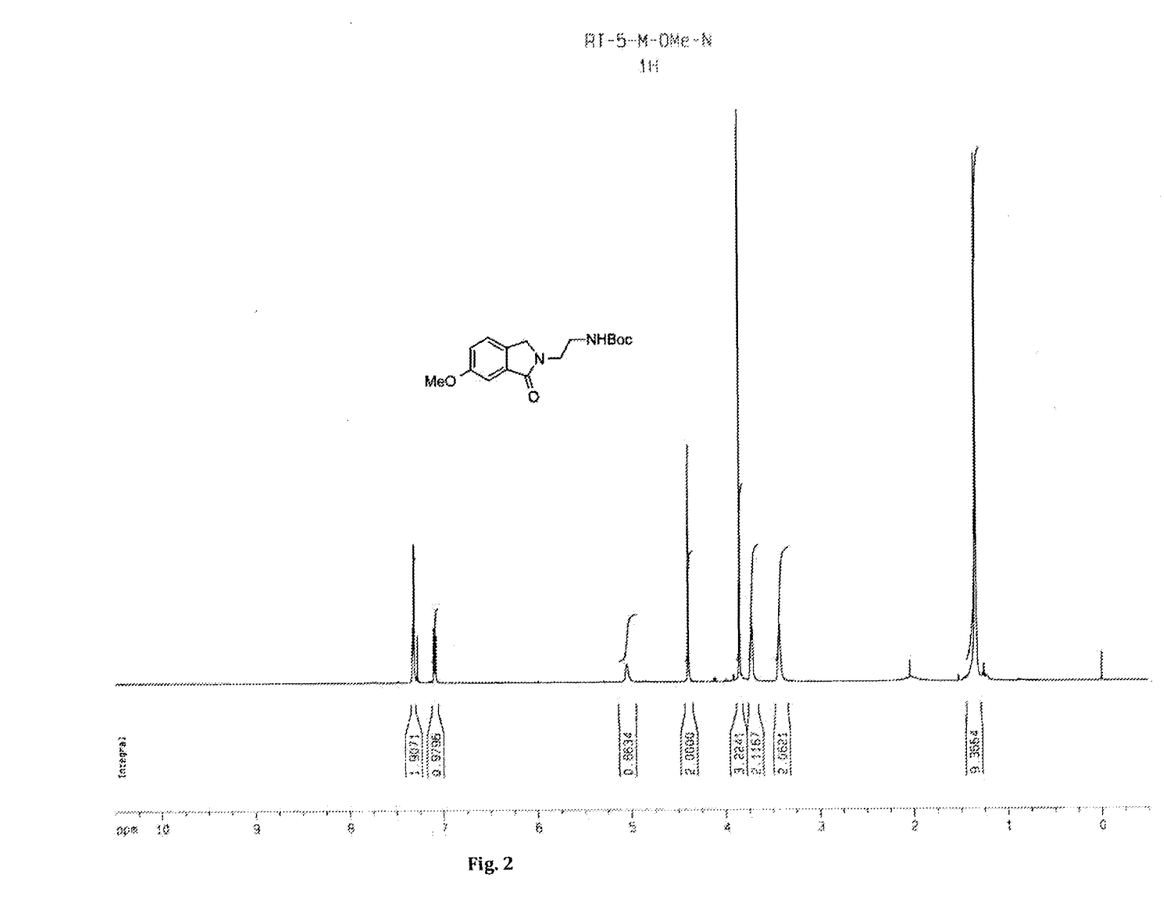
FIG. 2 is NMR spectrum of the reaction product from Example 1.

NH$_2$CH$_2$CH$_2$NHBoc was dissolved in PBS buffer (pH=7.4) at a concentration of 1 mM, compound 2 (1.2 equiv.) was added. The reaction mixture is stirred at room temperature for 1 h. The product was isolated by chromatography (%). $^1$H NMR (CDCl$_3$) δ 7.30 (2H, m), 7.05 (1H, m), 5.02 (1H, s), 4.30 (2H, s), 3.84 (3H, s), 3.80 (2H, m), 3.38 (2H, m), 1.28 (9H, s); $^{13}$C NMR (CDCl$_3$) δ 170.8, 161.4, 157.6, 135.2, 134.9, 125.0, 121.2, 107.8, 80.9, 57.1, 51.5, 43.9, 40.8, 29.8. (FIG. 2)

6.2 Example 2

Figure 3:
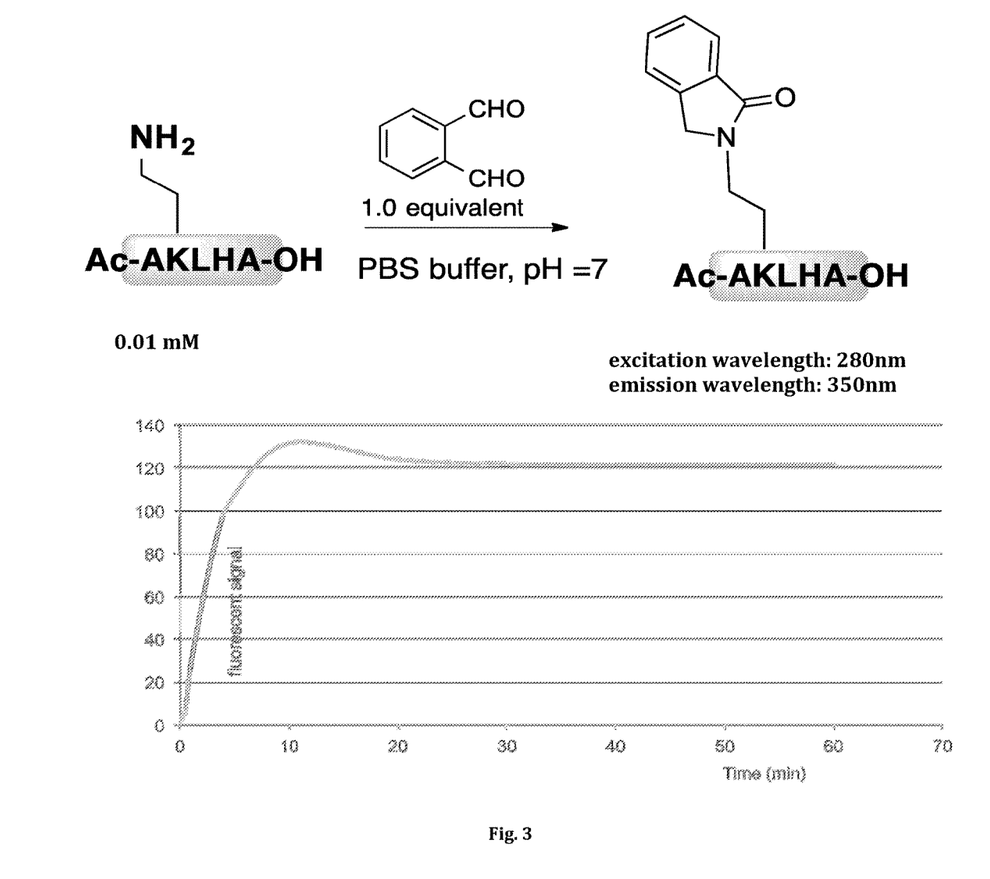
FIG. 3 illustrates the fluorescence turn-on properties of the method in Example 2.

As a model study, a peptide Ac-AKLHA-OH was prepared by solid phase peptide synthesis. A typical procedure for OPA/amine conjugation is as follows: to a solution of the lysine containing peptide in a PBS buffer (pH=7.4) at a concentration of 0.01 mM is added compound 1. The reaction mixture is stirred at room temperature. The reaction progress is monitored by measuring the fluorescence changes. The fluorescence intensity increased over time and reached the maximum at 10 min (FIG. 3). The product can be analyzed by LC-MS (FIG. 4). Ac-AKPHA-OH, ESI-MS, cal. M+H+: 546.4, found. 564; the product ESI-MS, cal. M+H+: 680.3, found 680.1.

6.3 Example 3

The present method is used in labeling and modifying native proteins. To demonstrate its effectiveness, BSA was conjugated with compound 10. BSA (albumin from bovine serum) was dissolved in PBS buffer (pH 7.4) at 1 mM, and next compound 10 was added to the above solution at 10 mM. The reaction mixture was incubated at room temperature for 1 hour. Then the protein was precipitated by acetone and the pellet was washed with methanol (X3). Next, the pellet was dissolved in the "click chemistry" buffer containing 1 mM TCEP (tris(2-carboxyethyl)phosphine), 0.1 mM TBTA (Tris(benzyltriazolylmethyl)amine) and 1 mM Cu$_2$SO$_4$. Azido-rhodamine (10 mM) was added to the above solution, and the reaction mixture was kept at room temperature for 3 hours. Acetone was added to precipitate the BSA protein. The pellet was washed with methanol (X3), and then dissolved in SDA-PAGE buffer and heated to 110° C. for 15 min SDS-PAGE was performed, and coomassie blue staining was compared with the fluorescence scan (FIG. 7).

6.4 Example 4

The conjugation method was further demonstrated by the PEGylation of BSA. To a solution of the BSA protein in PBS buffer (pH 7.4) at 1 mM was added compound 15 (See FIG. 5) (50 mM). The reaction mixture was incubated at room temperature for 5 min. The pellet from acetone precipitation was subjected to by MALDI-TOF Mass determination (FIG. 8). From the comparison, it is estimated that about 20 phthalaldehyde-PEG was conjugated onto BSA.

6.5 Example 5

Figure 9:
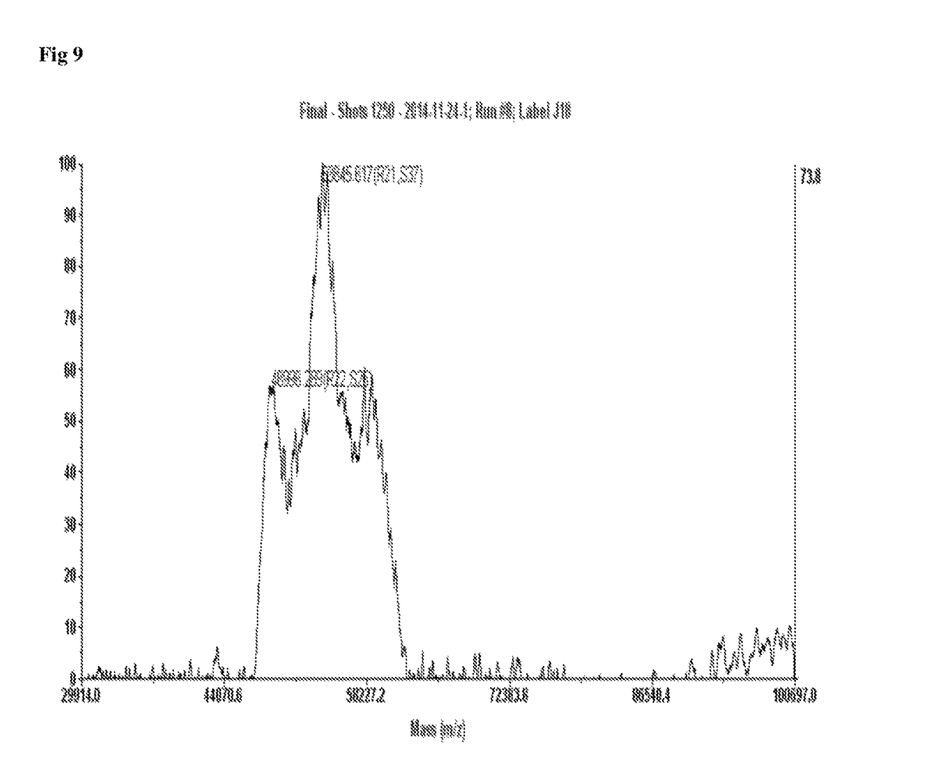
FIG. 9 is MALDI-TOF spectrum of PEPylation of L-asparaginase with compound 16.

L-asparaginase (0.25 mg) was dissolved in 30 μL PBS buffer (pH 7.4). To this solution, compound 16 (See FIG. 5) (0.76 mg, 20 equiv.) in PBS buffer was added. The mixture was stirred at room temperature for 2 hour. Methyl amino resin was added to quench the reaction. The filtrate was subjected to MALDI-TOF Mass determination (FIG. 9) which shows that 3-5 PEG was added to the protein.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A compound represented by formula (1), (1)

Wherein R' represents an amino acid residue, a peptide residue and/or a protein residue, and R represents H or at least one substituent.

2. The compound of claim 1, wherein said peptide residue is a synthetic or natural peptide residue.

3. The compound of claim 1, wherein said protein residue is a native protein residue or recombinant protein residue.

4. The compound of claim 1, wherein said protein residue is an enzyme residue or antibody residue.

5. The compound of claim 1, wherein said peptide residue comprises at least one lysine residue in the sequence.

6. The compound of claim 1, wherein said R is selected from alkyl, epoxide, amide, amine, ketone, aldehyde, phosphate, sulfate, halide, nitrile, nitro, azo, thiol, carboxylic acid, alkyne, ester, ether, alkene, or hydroxyl group.

7. The compound of claim 1, wherein said compound is obtained by reacting a compound represented by formula (2) with a compound represented by formula (3), (2)

(3)

Wherein R' represents an amino acid residue, a peptide residue and/or a protein residue, and R represents H or at least one substituent, said compound represented by formula (3) is selected from compounds 1 to 14:

1

2

3

4

5

6

7

-continued

8

9

10

11

12

13

-continued (14)

8. The compound of claim 1, wherein said R is linked with a poly(ethylene glycol) (PEG), a peptide, a drug, a carbohydrate, a fluorescent probe, DNA/RNA, a lipid, or combinations thereof.

9. A composition comprising a compound represented by the formula (1), (1)

Wherein R' represents an amino acid residue, a peptide residue and/or a protein residue, and R represents H or at least one substituent.

10. A kit comprising: (i) a compound represented by the formula (1), (1)

Wherein R' represents an amino acid residue, a peptide residue and/or a protein residue, and R represents H or at least one substituent; and (ii) a solvent.

* * * * *